United States Patent
Roeck et al.

(10) Patent No.: US 7,933,419 B2
(45) Date of Patent: Apr. 26, 2011

(54) IN-SITU-FITTED HEARING DEVICE

(75) Inventors: Hans-Ueli Roeck, Hombrechtikon (CH); Alfred Stirnemann, Zollikon (CH); Hans Leysieffer, Meilen (CH)

(73) Assignee: Phonak AG, Stafa (CH)

( * ) Notice: Subject to any disclaimer, the term of this patent is extended or adjusted under 35 U.S.C. 154(b) by 1587 days.

(21) Appl. No.: 11/243,587

(22) Filed: Oct. 5, 2005

(65) Prior Publication Data

US 2007/0076909 A1 Apr. 5, 2007

(51) Int. Cl.
*H04R 29/00* (2006.01)
(52) U.S. Cl. .......... 381/60; 381/314; 381/320; 381/321
(58) Field of Classification Search .............. 381/60, 381/312–331
See application file for complete search history.

(56) References Cited

U.S. PATENT DOCUMENTS

| | | | |
|---|---|---|---|
| 4,471,171 A | | 9/1984 | Kopke et al. |
| 4,972,487 A | * | 11/1990 | Mangold et al. ............. 381/315 |
| 4,989,251 A | * | 1/1991 | Mangold ........................ 381/314 |
| 5,266,919 A | * | 11/1993 | Cook et al. .................. 340/384.7 |
| 5,991,417 A | | 11/1999 | Topholm |
| 6,118,877 A | * | 9/2000 | Lindemann et al. ............. 381/60 |
| 6,175,635 B1 | * | 1/2001 | Meyer et al. .................. 381/314 |
| 6,668,204 B2 | | 12/2003 | Neoh |
| 6,674,862 B1 | | 1/2004 | Magilen |
| 6,826,286 B1 | * | 11/2004 | Arndt et al. ................... 381/312 |
| 6,850,775 B1 | | 2/2005 | Berg |
| 7,006,646 B1 | * | 2/2006 | Baechler ....................... 381/314 |
| 7,058,182 B2 | * | 6/2006 | Kates ............................... 381/60 |
| 7,242,778 B2 | * | 7/2007 | Csermak et al. ................ 381/60 |
| 2003/0122578 A1 | | 7/2003 | Masui et al. |
| 2004/0165731 A1 | * | 8/2004 | Ribic ............................... 381/60 |
| 2004/0190739 A1 | | 9/2004 | Bachler et al. |
| 2005/0129262 A1 | | 6/2005 | Dillon et al. |
| 2005/0259829 A1 | * | 11/2005 | Van den Heuvel et al. ..... 381/60 |

FOREIGN PATENT DOCUMENTS

| | | |
|---|---|---|
| EP | 1 301 060 A1 | 4/2003 |
| EP | 1 414 271 A2 | 2/2004 |
| EP | 1414271 A2 | 4/2004 |
| WO | WO 99/49715 | 7/1999 |
| WO | 9948323 A2 | 9/1999 |
| WO | WO 00/44198 | 7/2000 |

OTHER PUBLICATIONS

European Office action for 05 021 704.0-2225 dated Jun. 21, 2010.

* cited by examiner

*Primary Examiner* — Curtis Kuntz
*Assistant Examiner* — Ryan Robinson
(74) *Attorney, Agent, or Firm* — Pearne & Gordon LLP

(57) ABSTRACT

The hearing device is operable in a fitting mode and in a listening mode and comprises a transducer for receiving, in the fitting mode, audio test signals, and for converting the audio test signals into signals to be perceived by the user in the fitting mode. It comprises a parameter memory means for storing parameter settings, which parameter settings are obtained from user input received through a user interface in response to the signals perceived by the user in the fitting mode. And it comprises a signal processor using the parameter settings for correcting audio signals at least in the listening mode. The user interface is comprised in the hearing device and the hearing device comprises an audio signal source, in which audio signal source the audio test signals are stored or generated.

21 Claims, 2 Drawing Sheets

IN-SITU-FITTED HEARING DEVICE

BACKGROUND OF THE INVENTION

1. Field of the Invention

The invention relates to a hearing device, which can be fitted to a user's hearing preferences, and to a method for fitting a hearing device. The hearing device can be a hearing aid, worn in or near the ear or implanted, a headphone, an earphone, a hearing protection device, a communication device or the like.

2. Description of Related Art

From U.S. Pat. No. 6,668,204 two-channel hearing devices, in particular a headphone and a hearing aid, are known, which can be adapted to a user's hearing preferences or hearing imperfections, more particularly to compensate for differences between the perception in the left and the right ear. The hearing device can be connected to a personal computer, which personal computer has a user interface and contains a sound source as well as computation means. The user can choose a frequency and will thereupon hear an according sound from the sound source, downloaded to the hearing device. Via the user interface the user can then adjust the balance at that frequency until the sound is perceived centered between the left and right channels. This can be done for different frequencies, and thereafter the user can equalize the system to compensate for perceived differences in amplitude between different frequencies. After that, compensation coefficients are obtained by means of the personal computer. The compensation coefficients can be downloaded to the hearing device and can be used by a signal processor for providing for real-time equalization for each ear, so as to obtain corrected analog audio signals according to the user's hearing preferences.

In US 2003/0133578 A1 a hearing aid is presented, which can be audio-fitted by the user himself. The user can make pairwise comparisons between parameter settings (settings of gains, compression ratios, frequency values and the like) by toggling between the two different settings, and then choose that one setting which provides him with the better listening experience. Numerous such pairwise comparisons are necessary. By means of a genetic algorithm the numerous preferences, as derived from the user's choices, are converged and result in a single solution, which is expected to precisely fit the user's hearing needs.

The fitting procedure disclosed in US 2003/0133578 A1 requires to store a very large number of finally unused parameter settings. In addition, this fitting procedure is expected to take a considerable amount of time, due to the large number of required comparisons.

BRIEF SUMMARY OF THE INVENTION

An object of the invention is to provide for a hearing device, which can easily be fitted to a user's needs without or largely without additional means.

Another object of the invention is to provide for a hearing device, which can easily be fitted to a user's needs fully or at least in major parts by the user himself.

Another object of the invention is to provide for a hearing device, which can be fitted to a user's needs without or substantially without the help of a professional hearing device fitter.

Another object of the invention is to provide for a hearing device, which can be fitted to a user's needs even when no personal computer or similar means is available.

Another object of the invention is to provide for a hearing device, which can be reasonably well fitted to a user's needs within a relatively short period of time.

Another object of the invention is to provide for a hearing device, which can be fitted to a user's needs, wherein main time-consuming steps during the fitting can be performed by the user himself.

Another object of the invention is to provide for a hearing device, which can be fitted to a user's needs without measuring an audiogram or middle ear reflexes or brainstem responses or the like.

Another object of the invention is to provide for a hearing device, which can be fitted to a user's needs and requires only little memory space for storing parameter settings.

Another object of the invention is to provide for a hearing device, which can be fitted to a user's needs and does not have to store a large number of finally unused parameter settings.

Another object of the invention is to provide for a method for fitting a hearing device to a user's needs without or largely without additional means.

Another object of the invention is to provide for a method for fitting a hearing device to a user's needs fully or largely by the user himself.

Another object of the invention is to provide for a method for fitting a hearing device to a user's needs without or substantially without the help of a professional hearing device fitter.

Another object of the invention is to provide for a method for fitting a hearing device to a user's needs even when no personal computer or similar means is available Another object of the invention is to provide for a method for fitting a hearing device to a user's needs within a relatively short period of time.

Another object of the invention is to provide for a method for fitting a hearing device to a user's needs, wherein main time-consuming steps during the fitting can be performed by the user himself.

Another object of the invention is to provide for a method for fitting a hearing device to a user's needs without measuring an audiogram or middle ear reflexes or brainstem responses or the like.

Another object of the invention is to provide for a method for fitting a hearing device to a user's needs while using only little memory space for storing parameter settings.

Another object of the invention is to provide for a method for fitting a hearing device to a user's needs without storing a large number of finally unused parameter settings.

These objects are achieved by a hearing device and by a method for fitting a hearing device according to the patent claims.

The hearing device is operable in a fitting mode and in a listening mode, and the device comprises

- a transducer for receiving, in the fitting mode, audio test signals, and for converting the audio test signals into signals to be perceived by a user of the hearing device in the fitting mode;
- a user interface;
- a parameter memory means for storing parameter settings, which parameter settings are obtained from user input received through the user interface in response to the signals perceived by the user in the fitting mode;
- a signal processor using the parameter settings for correcting audio signals at least in the listening mode; and
- an audio signal source, in which the audio test signals are stored or generated.

This way a stand-alone fitting (audio-fitting) of the hearing device can be achieved. The hearing device can be adapted to the user's hearing needs in-situ and without additional means like a personal computer or an external module. The hearing device can be fitted autonomously by, the user.

A hearing device can be, e.g., a hearing aid, worn in or near the ear or implanted, a headphone, an earphone, a hearing protection device, a communication device. The hearing device may comprise a remote control, an add-on device like, e.g., a radio frequency receiver pluggable onto an ear piece of the hearing device, or other associated devices belonging to the hearing device.

The hearing device may comprise means for obtaining parameter settings from the user input. This means can, e.g., be an algorithm implemented in a software or in a signal processor. This can make the fitting fully independent from external software and external devices like personal computers. The means contains the rules for obtaining parameter settings from the user input. The means for obtaining parameter settings can comprise look-up tables and/or rules for an interpolation between pre-programmed parameter settings.

In one embodiment, the transducer is also used for receiving, in the listening mode, audio signals, and for converting the audio signals into signals to be perceived by the user in the listening mode. This way, the transducer is used in the fitting mode as well as in the listening mode, which not only allows to design the hearing device more compact, but also improves the quality of the fitting, since possible differences between one transducer used in the fitting mode and another transducer used in the listening mode are intrinsically eliminated.

In another embodiment, the user interface has controls, which are, at least in part, identical with controls of the hearing device to be used by the user in the listening mode. This allows for a more compact design of the hearing device.

The hearing device may comprise a remote control or another separatable device, and such a device may comprise, fully or in part, the user interface. Such a separable device may also comprise, fully or in part, the audio signal source and/or the parameter memory means.

In another embodiment, the signal processor uses the parameter settings for correcting audio signals in the fitting mode and in the listening mode. An increased quality of the fitting can be achieved if those parameters are used in the listening mode, which have been obtained from and used in the fitting mode.

In another embodiment, the parameter settings comprise values for gains for at least one or at least two or at least three different frequency bands. Gains for different frequency bands are often times important parameters, in particular in hearing aids. And the influence of such gains can usually be reasonably well judged by an average user.

In another embodiment, the audio test signals comprise signals representing sounds known to the user from everyday life. Those sounds shall stem from the environment the user (or a typical user) lives in. Due to such "natural" (not artificial) sounds the user will be able to automatically adapt his hearing device in a way that the user will consider the overall sound as pleasant. Thus a significant part of a fine-tuning of the hearing device is readily achieved. In one embodiment, digitally sampled sounds are comprised in the audio test signals.

In another embodiment, the audio test signals comprise speech signals. In particular, the speech signals can (also) be used for guiding the user in the fitting mode. This way, a comfortable guidance of the user during the fitting (prompting for user input) can be achieved.

Oftentimes, the signals to be perceived by the user in the fitting mode are acoustical sound. If, for example, the hearing device is (partially) implanted, the signals to be perceived by the user in the fitting mode can be electrical signals for stimulating a nerve.

Typically, the hearing device, or at least a part of it, is to be worn by the user in or near the user's ear.

The hearing device may comprise, in addition to an ear piece, which is a part of the hearing device to be worn by the user in or near the user's ear, a separable device. Such a separable device may be or comprise a remote control.

In another embodiment, the hearing device comprises a means for recording, during the listening mode, user input received through controls of the hearing device used in the listening mode. This is very advantageous for a further fine-tuning of the hearing device, which may be done with an external device for evaluating the recorded data, or within the hearing device. In one embodiment, the hearing device comprises means for obtaining parameter settings from the user input recorded in the listening mode. In that case, an in-situ and autonomous fine-tuning of the acoustic properties of the hearing device can be performed. The means for obtaining parameter settings from the recorded user input can, e.g., be programmed such that, if the user of, e.g., a hearing aid has repeatedly reduced the volume (using, e.g., a volume dial) in some acoustical environments, in which a certain frequency band is predominant, the gain for that frequency band will be reduced.

The method for fitting a hearing device, which is operable in a fitting mode and in a listening mode, comprises, in the fitting mode, the steps of
    converting audio test signals stored or generatable in the hearing device into signals to be perceived by a user of the hearing device;
    receiving user input via a user interface of the hearing device in response to the signals perceived by the user;
    obtaining parameter settings from the user input, which parameter settings are to be used for correcting audio signals in the listening mode; and
    storing the parameter settings in the hearing device.

In one embodiment, the method comprises furthermore the step of choosing initial parameter settings, which may include at least one initial gain value and at least one initial compression value, upon a description of the user's hearing situation. Said initial parameter settings may, e.g., be chosen by manipulating at least one control of the user interface during a booting process (switching on) of the hearing device. Or said hearing devices are available with one of various pre-programmed parameter settings (presets), and on the hearing device itself or on a hearing device's package an indication or labelling identifying the initial parameter settings is provided, e.g., an imprinted "1" or "2" or "3", wherein, e.g., in the case of a hearing aid, "1" could indicate an initial parameter setting for a user with light hearing loss, "2" could indicate an initial parameter setting for a user with moderate hearing loss, and "3" could indicate an initial parameter setting for a user with severe hearing loss. Depending on the description of the user's hearing situation, a hearing aid with suitable preset initial parameter settings could be chosen. Said description of the user's hearing situation can, e.g., be provided orally or in writing by the user, who reports, e.g., in the case of a hearing aid, e.g., which kind of everyday-life sounds he perceives under which circumstances. And/or said description of the user's hearing situation can, e.g., be obtained by exposing the user (at that time not provided with the hearing device), with known acoustic stimuli (e.g., sounds from a musical instrument, or sounds played to the user via loudspeakers) and determine therefrom the user's hearing situation (degree of a possible hearing loss, possible problems with high frequencies, typical hearing situations the user is exposed to, and the like).

In one embodiment, of the method the audio test signals comprise at least a first and a second test signal, the spectral contents of which, when converted into signals to be perceived by the user, are substantially representative of a first and a second spectral band, respectively, which first and a second spectral bands are substantially different, i.e., the spectral bands do not or only partially (to a small extent) overlap. This allows for an efficient way of finding suitable values for gains for different frequency bands.

In another embodiment, in the fitting mode, firstly
the first test signal is converted into a first signal to be perceived by the user; and
the user input in response to the first signal comprises increasing or decreasing the perceived loudness of the first perceived signal;
and secondly
the second test signal is converted into a second signal to be perceived by the user; and
the user input in response to the second signal comprises increasing or decreasing the perceived loudness of the second perceived signal;
wherein
from the user input in response to the first signal and from the user input in response to the second signal at least one gain value for the amplification of the first spectral band and at least one gain value for the amplification of the second spectral band is obtained.

The increasing or decreasing the perceived loudness of the (first and second) perceived signal will usually be accomplished by adjusting the volume control of the user interface appropriately. It is possible to foresee that the user, by manipulating a control of the user interface, e.g., pressing a switch, acknowledges to the hearing device that the correct volume setting is adjusted.

Advantages of methods correspond to the advantages of corresponding hearing devices and vice versa.

Further embodiments and advantages emerge from the dependent claims and the figures.

BRIEF DESCRIPTION OF THE DRAWINGS

Below, the invention is illustrated in more detail by means of embodiments of the invention and the included drawings.

The figures show.

The reference symbols used in the figures and their meaning are summarized in the list of reference symbols. Generally, alike or alike-functioning parts are given the same or similar reference symbols. The described embodiments are meant as examples and shall not confine the invention.

DETAILED DESCRIPTION OF THE INVENTION

Figure 1:
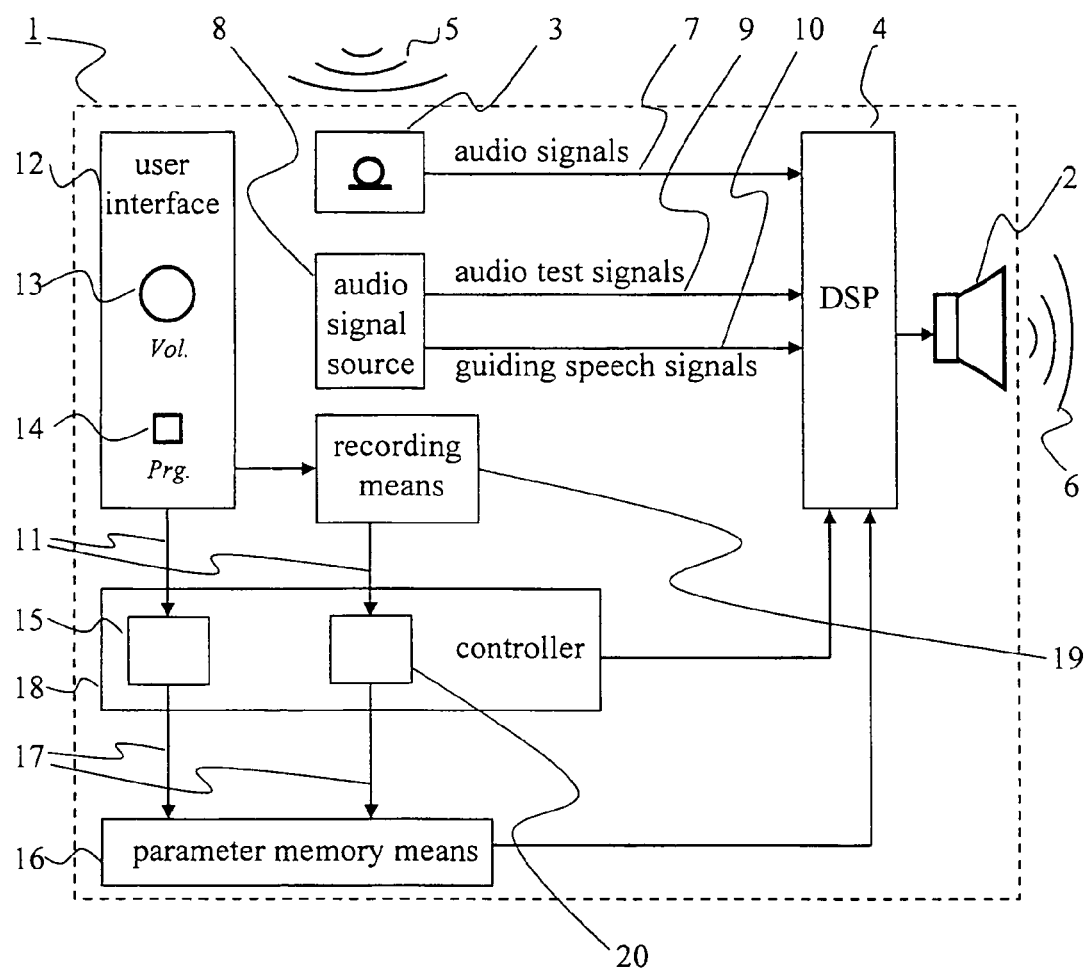
FIG. 1 a schematic diagram of a hearing device.

FIG. 1 shows a schematic diagram of a hearing device 1, which is operable in a fitting mode and in a listening mode. The hearing device 1 can be considered a hearing aid. The listening mode is the normal mode of operation, in which incoming sound 5 is received by a microphone 3 of the hearing device 1, converted into audio signals 7, which can be processed and/or corrected in a usually digital signal processor 4 (DSP) and, after amplification (not shown in FIG. 1), be converted, by means of a loudspeaker 2, into sound 6 to be perceived by a user of the hearing device 1.

In the fitting mode, parameter settings 17 shall be found, which are used in the DSP 4 during the listening mode, so that the signal 6 provided to the user is adapted to the user's hearing requirements. Such parameter settings may include, but are not limited to, one or more of the group consisting of overall amplification gain, gains for different frequency bands, compression ratios (at different input levels), expansion ratios, frequency values like sampling frequencies, filter crossover frequencies, time constants, output limiting threshold values.

The hearing device comprises an audio signal source 8, which contains or generates audio test signals 9, which can be, optionally after having been processed in the DSP 4, fed into the loudspeaker (transducer) 2 in order to generate signals 6 to be perceived by the user. Step 100 of the block diagram of FIG. 2, which depicts steps performed in the fitting mode, illustrates this.

Figure 2:
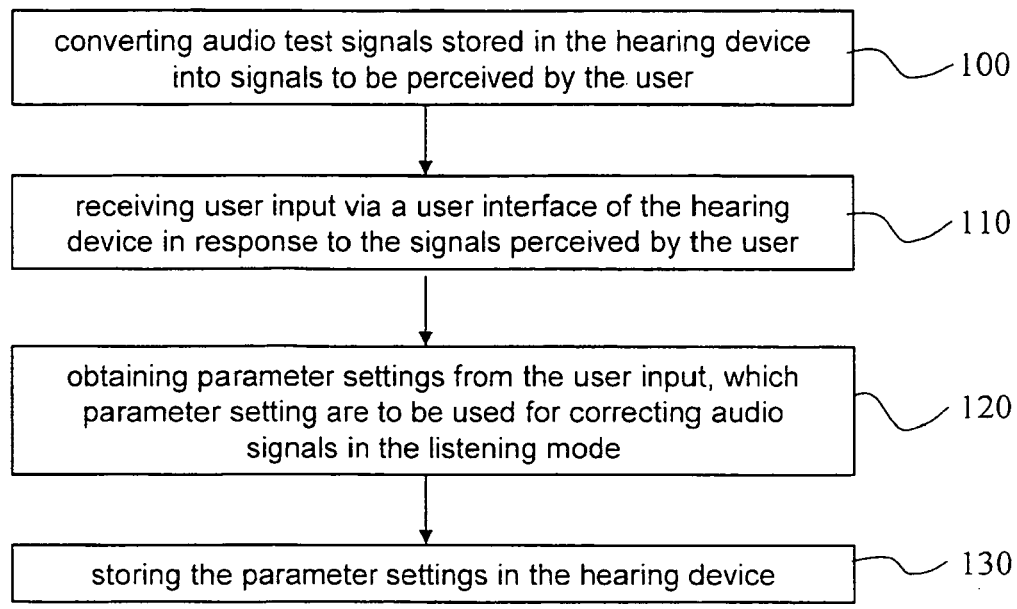
FIG. 2 a block diagram of a method to operate a hearing device in the fitting mode.

Upon perceiving the signals 6, the user can respond to that by using a user interface 12 of the hearing device 1. In the hearing device of FIG. 1 the user interface 12 for use in the fitting mode is identical with the user interface, which the user uses in the listening mode. The user interface 12 comprises controls 13,14, which are identical with a volume wheel 13 and a program change knob 14. If, e.g., the user perceives the sound 6 as too loud or too soft, he can manipulate the volume wheel 13 until the sound 6 is perceived in a pleasant volume. Step 110 of FIG. 2 depicts this step.

From the user's input 11 in response to one or several perceived signals 6 parameter settings 17 can be obtained through a means 15 for obtaining parameter settings from user input. The means 15 can, e.g., be integrated in a controller 18 of the hearing device 1. Step 120 of FIG. 2 depicts this step.

Parameter settings 17 can be stored in a parameter memory means 16 of the hearing device 1. Step 130 of FIG. 2 depicts this step. The (new) parameter settings 17 will then be used in the DSP 4 in the listening mode and, optionally, also in the fitting mode.

It will usually be sufficient to store one or two parameter settings 17 in the hearing device 1. If the hearing device has several hearing programs (usually for different incoming signals 5), storing one or two parameter settings 17 per hearing program in the hearing device will usually be sufficient.

At least a part of the audio test signals 9 stored in the audio signal source 8 can be sounds known to the user from everyday life. E.g., a triangle sound, some telephone speech and a ship horn could be suitable sounds. In one embodiment, at least part of the audio test signals 9 are digitally sampled sounds.

In one embodiment, at least a subset of the audio test signals 9 are sounds representative of a specific spectral band each, which spectral bands may be partially overlapping or subtantially not overlapping. Accordingly, the sounds are selected so as to contain sufficient spectral density within the appropriate frequency band. The three sounds mentioned above can be considered as a set of sounds representative for a high frequency band (triangle), a medium frequency band (telephone speech) and a low frequency band (ship horn), respectively. Their spectral bands are substantially not overlapping with the exception that the low frequency band of the ship horn partially overlaps with the medium frequency band.

Example for a relatively basic fitting procedure:

A long press on the program change button 14 may toggle between the listening mode and the fitting mode. Upon entering the fitting mode, the triangle sound is played to the user (possibly repeatedly). The user manipulates the control 13 (volume wheel) until a comfortable audibility of the sound is achieved. Pressing the control 14 (shortly) will change to the middle frequency band; the telephone speech sound will be played to the user. Again, the user will manipulate the control 13 (volume wheel) until a comfortable audibility of the sound is achieved. Another (short) press on the control 14 will initiate the same actions for the low frequency band. It may be foreseen that nother (short) press on the control 14 leads back to the high frequency sound. Finally, a long press on control 14 can initiate the calculation and storing of the new parameter settings 17, which in that case would at least comprise one gain value for each of the three frequency bands represented by the three sounds. The listening mode is engaged, and the new (improved) parameters are used.

It is also possible to calculate new parameter settings 17 immediately after each (short) press on the control 14 and to use the new parameter settings 17 from then on (already during the fitting).

In one embodiment, the audio signal source 8 comprises guiding speech signals 10, which also is depicted in FIG. 1. Such signals may be synthezised or be sound samples of the human voice. The guiding speech signals 10 can be used in the fitting mode and possibly also in the listening mode. In the fitting mode the user will be guided through the fitting procedure by instructions given through the guiding speech signals 10. E.g., "Please adjust the volume" or "If you want to terminate the fitting procedure, press and hold the button" or the like.

The guiding speech signals 10 (or a part of them) can, at the same time, be used as audio test signals 9.

Another feature is depicted in FIG. 1 in conjunction with the items 19 and 20. It is possible to foresee a recording means 19 in the hearing device 1 for recording, during the listening mode, user input received through controls 13,14 of the hearing device 1 used in the listening mode. I.e., when in listening mode, the user will from time to time, usually depending on the acoustical environment in which he is, make manipulations with controls of the hearing device, which are meant for such purposes. E.g., the user will reduce the volume by means of the volume wheel 13 when the perceived overall volume is too high. Such user input may be recorded constantly, periodically or upon request, in the recording means 19. Constantly, periodically or upon request, possibly also with the aid of an external computer or similar device, the recorded data can be evaluated, and through a means 20 for obtaining parameter settings from the user input recorded in the listening mode new parameter settings 17 can be obtained.

For example, the hearing device may record sound situations (e.g., in form of amplitude histograms over frequency) and the thereby performed volume changes as made by the user through the volume control. The recorded information may then be used to adapt gain settings or other parameters upon turning on the hearing device or upon changing into a certain hearing device program used in a respective sound situation.

"Intelligent" changes in parameter settings may be forseen, like, e.g., turning on a beamformer for focused reception of sound 5 in a speech-in-noise environment instead of increasing a gain value, when the user repeatedly requests a higher volume via the volume wheel in such acoustical situations.

Thus the hearing device may learn from the actions (manipulations of the controls of the hearing device) of the user and takes his sound perception in real day-to-day situations into account.

In EP 1 414 271 A2 and US 2004/0190739 A1 it is described in great detail, how such information may be recorded and evaluated. Therefore, EP 1 414 271 A2 and US 2004/0190739 A1 are herewith incorporated by reference in this application.

The means 15 and 20 may be identical. One or both of the means 15 and 20 may be part of the controller 18. The controller 18 may be partially or in full be integrated in the DSP 4. The parameter memory means 16 may partially or in full be integrated in the DSP 4 or in the controller 18.

The incoming signal 5 may be sound 5 or electromagnetic waves to be received by the hearing device 1 (e.g., wireless headphone, implanted hearing aid with wireless transmitter (wireless reception), or hearing aid in the respective mode).

Before the actual fitting and before the insertion of the hearing device 1 or a part of the hearing device 1 into the user's ear (if the hearing device 1 is designed accordingly), it is possible to add an inspection step, in which a fundamentally-educated person inspects the user's ear for obstructions.

Furthermore, it is possible to choose initial parameter settings, in particular initial gain settings, e.g., according to a user's self-described hearing problem (e.g., light loss, moderate loss, severe loss) by either choosing from a number of hearing devices a hearing device with pre-set parameter settings for the described hearing problem, which can, e.g. be labeled on a packaging of the hearing device, or set the parameter settings through a (simple) selection procedure via the user interface.

It is possible to use the above-described fitting method (cf. FIG. 2) as the only audio-fitting to be done with the hearing device. In that case it is possible to use at no stage an additional device not belonging to the hearing device during fitting the hearing device. It is, alternatively, possible to use that method as a part of a more extensive fitting. In that case, it is possible to add more elaborate fitting steps, which, e.g., may make use of software on an external personal computer.

The use of "natural" sounds (sounds already known to the user) not only has the advantage that the user's acceptance of such sounds is great and that the user readily feels comfortable with such sounds (as opposed to sine waves or the like, which are often used in fitting procedures). Since such "natural" sounds are never extremely narrowband, e.g. sinusoidal, a certain interpolation over different frequency bands can automatically be achieved. Nevertheless, it is possible to interpolate or extrapolate parameter settings for additional (e.g., intermediate) frequency bands from the settings for a smaller number of actually tested frequency bands like the three bands discussed above. Known frequency relationships like known partial transfer functions like RECD (real-ear-to-coupler difference), MLE (microphone location effect), OEG (open ear gain) and others may be incorporated in the derivation of gain parameters. An MPO (maximum power output) may initially or generally be set to standard values for unimpaired persons (e.g., 100 dB) or may be automatically adapted according to the user-defined gain settings, or may be set by the user either explicitly (upon tests with appropriate test audio signals) or implicitly (through evaluation of the user's manipulations of the user interface during listening mode as described above).

Any or a group of the parameters knee-point levels, knee-point gains, expansion slopes, compression slopes, maximum gain settings, maximum output values, and other parameters may be pre-configured or derived from the parameter settings obtained from the user input.

Figure 3:
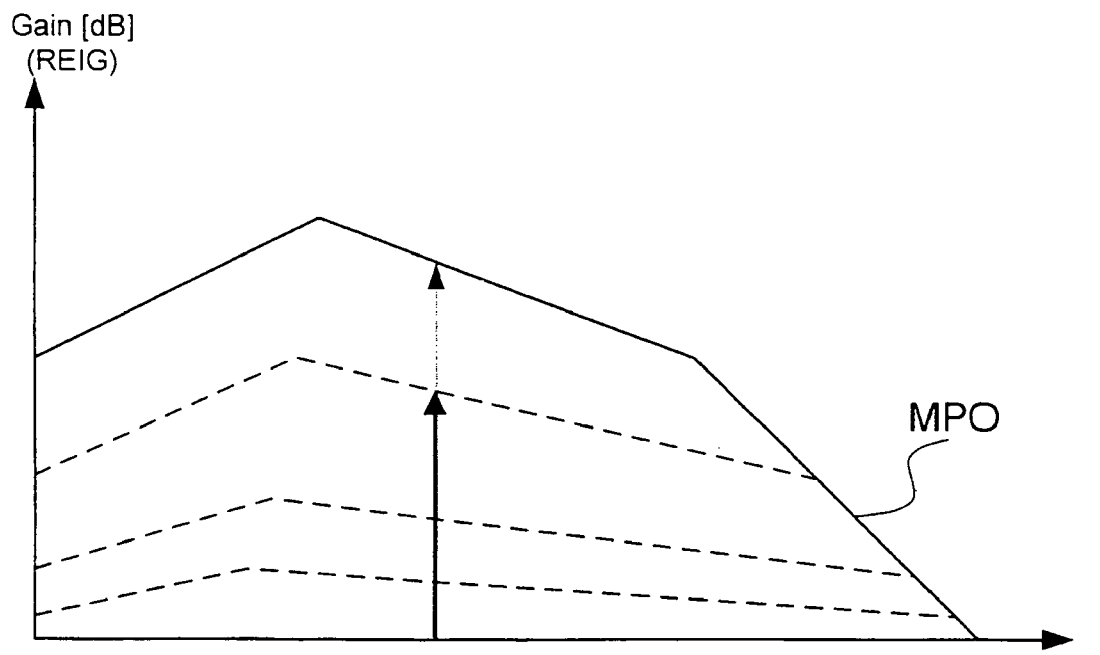
FIG. 3 Real-Ear Insertion Gain for one frequency band in dependence of the input power and its changes with changes in the overall volume.

FIG. 3 schematically shows an example for a pre-configured REIG (real-ear insertion gain) (in dB), e.g., for one frequency band, dependent on the input power (in dB signal pressure level) and how it changes with changes in the overall volume as selected by the user. The solid curve depicts the MPO, which is used when the volume is set to maximum by means of the volume dial (thin dotted arrow). Upon reducing the volume somewhat (as indicated by the thick solid arrow), the REIG curve is changed to the uppermost dashed curve in FIG. 3. REIG curves for even lower chosen volumes are also shown.

LIST OF REFERENCE SYMBOLS 1 hearing device, hearing aid
2 transducer, output transducer, loudspeaker, receiver
3 transducer, input transducer, microphone
4 signal processor, digital signal processor, DSP
5 sound, incoming sound, incoming signal (listening mode)
6 signals to be perceived by the user (in the fitting mode or in the listening mode), sound, outgoing sound
7 audio signals (listening mode)
8 audio signal source
9 audio test signals
10 guiding speech signals
11 user input
12 user interface, set of controls
13 control, volume wheel
14 control, program change knob
15 means for obtaining parameter settings from user input; part of controller
16 parameter memory means, memory chip
17 parameter settings, set of audio parameters
18 controller
19 recording means, means for recording, during the listening mode, user input received through controls of the hearing device used in the listening mode
20 means for obtaining parameter settings from the user input recorded in the listening mode
100-130 steps

The invention claimed is:

1. Hearing device operable in a fitting mode and in a listening mode, said device comprising
   an output transducer for receiving, in the fitting mode, audio test signals, and for converting the audio test signals into signals to be perceived by a user of the hearing device in the fitting mode;
   a user interface comprising a volume controller that is operable during the listening mode for controlling volume during the listening mode;
   a parameter memory means for storing parameter settings, wherein the parameter settings, which are values assigned to respective parameters, are derived from user input received through the volume controller in the fitting mode, in response to the signals perceived by the user in the fitting mode;
   a signal processor configured for using the parameter settings for correcting audio signals in the fitting mode and in the listening mode; and
   an audio signal source, in which the audio test signals are stored or generated.

2. The device according to claim 1, furthermore comprising a means for obtaining parameter settings from the user input.

3. The device according to claim 1, wherein the output transducer is also used for receiving, in the listening mode, audio signals, and for converting the audio signals into signals to be perceived by the user in the listening mode.

4. The device according to claim 1, wherein the user interface has controls, which are, at least n part, identical with controls of the hearing device to be used by the user in the listening mode.

5. The device according to claim 1, wherein the parameter settings comprise values for gains for at least two different frequency bands.

6. The device according to claim 1, wherein the audio test signals comprise signals representing sounds known to the user from everyday life.

7. The device according to claim 1, wherein the audio test signals comprise digitally sampled sounds.

8. The device according to claim 1, wherein the audio test signals comprise speech signals.

9. The device according to claim 1, wherein the audio test signals comprise speech signals for guiding the user in the fitting mode.

10. The device according to claim 1, wherein the signals to be perceived by the user in the fitting mode are sound.

11. The device according to claim 1, wherein the hearing device is to be worn by the user in or near the user's ear.

12. The device according to claim 1, wherein the hearing device comprises a remote control.

13. The device according to claim 1, which hearing device comprises a means for recording, during the listening mode, user input received through controls of the hearing device used in the listening mode.

14. The device according to claim 13, which hearing device comprises means for obtaining parameter settings from the user input recorded in the listening mode.

15. The device according to claim 1, wherein the parameter settings are derived from a selectable user input level received through the user interface in the fitting mode.

16. The device according to claim 2, wherein the means for obtaining parameter settings from the user input contains rules for obtaining parameter settings from the user input.

17. The device according to claim 1, wherein the parameter settings comprise one or more of the group consisting of
   values for gains for at least two different frequency bands;
   values for compression ratios;
   values for compression ratios at different input levels;
   values for expansion ratios;
   values for frequency values;
   values for sampling frequencies;
   values for filter crossover frequencies;
   values for time constants; and
   output limiting threshold values.

18. A method, comprising the steps of:
   providing the hearing device of claim 1, the method further comprising, in the fitting mode, the steps of;
   converting the audio test signals stored or generated in the hearing device into the signals to be perceived by the user of the hearing device;
   receiving the user input via the user interface in response to the signals perceived by the user;
   obtaining the parameter settings from the user input, which parameter settings are to be used for correcting audio signals in the fitting mode and in the listening mode; and
   storing the parameter settings in the hearing device.

19. Method according to claim 18, further comprising the step of choosing initial parameter settings, which include at least one initial gain value and at least one initial compression value, upon a description of the user's hearing situation.

20. Method according to claim 18, wherein the audio test signals comprise at least a first and a second test signal, the spectral contents of which, when converted into the signals to be perceived by the user, are substantially representative of a first and a second spectral band, respectively, said first and second spectral bands are substantially different.

21. Method according to claim 20, wherein, in the fitting mode, firstly the first test signal is converted into a first signal to be perceived by the user; and a user input in response to the first signal comprises increasing or decreasing the perceived loudness of the first signal;

and secondly the second test signal is converted into a second signal to be perceived by the user;

a user input in response to the second signal comprises increasing or decreasing the perceived loudness of the second signal;

wherein from the user input in response to the first signal and from the user input in response to the second signal at least one gain value for amplification of the first spectral band and at least one gain value for amplification of the second spectral band are obtained.

\* \* \* \* \*

UNITED STATES PATENT AND TRADEMARK OFFICE
CERTIFICATE OF CORRECTION

| | | |
|---|---|---|
| PATENT NO. | : 7,933,419 B2 | Page 1 of 1 |
| APPLICATION NO. | : 11/243587 | |
| DATED | : April 26, 2011 | |
| INVENTOR(S) | : Hans-Ueli Roeck et al. | |

It is certified that error appears in the above-identified patent and that said Letters Patent is hereby corrected as shown below:

In the claims, column 10, line 6, replace "n" with -- in --

Signed and Sealed this
Twenty-sixth Day of July, 2011

David J. Kappos
*Director of the United States Patent and Trademark Office*